United States Patent
Kinpara (10) Patent No.: US 9,114,066 B2
(45) Date of Patent: Aug. 25, 2015

(54) FISTULA CATHETER AND RELATED METHODS THEREFOR

(75) Inventor: Yuichi Kinpara, Shizuoka (JP)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/342,809

(22) PCT Filed: Sep. 13, 2012

(86) PCT No.: PCT/US2012/055019
§ 371 (c)(1),
(2), (4) Date: Aug. 8, 2014

(87) PCT Pub. No.: WO2013/040133
PCT Pub. Date: Mar. 21, 2013

(65) Prior Publication Data
US 2014/0371680 A1    Dec. 18, 2014

(30) Foreign Application Priority Data
Sep. 14, 2011    (JP) .................................. 2011-201071

(51) Int. Cl.
*A61J 15/00* (2006.01)
*A61M 25/02* (2006.01)

(52) U.S. Cl.
CPC .......... *A61J 15/0038* (2013.01); *A61J 15/0015* (2013.01); *A61J 15/0065* (2013.01); *A61J 15/0007* (2013.01); *A61J 15/0061* (2013.01); *A61M 2025/0233* (2013.01)

(58) Field of Classification Search
CPC . A61J 5/0038; A61J 15/0015; A61J 15/0065; A61J 15/0061; A61M 2025/0233
USPC ....................................................... 604/174
See application file for complete search history.

(56) References Cited

U.S. PATENT DOCUMENTS 1,588,344 A * 6/1926 Varney ........................... 604/107
2001/0056273 A1 12/2001 Ewers
(Continued)

FOREIGN PATENT DOCUMENTS

| EP | 1025802 A1 | 8/2000 |
|---|---|---|
| EP | 1623693 A1 | 2/2006 |

(Continued)

OTHER PUBLICATIONS

International Preliminary Report on Patentability dated Mar. 18, 2014 for corresponding PCT Application No. PCT/US2012/055019.
(Continued)

*Primary Examiner* — Manuel Mendez (57) ABSTRACT

A fistula catheter which can be inserted and withdrawn without the use of a replacement tool such as a syringe or an extension tool and a fistula catheter that is sparingly invasive for the fistula are disclosed.

The fistula catheter can have a substantially cylindrical catheter part; a rod-like bumper part; a guide part provided with a flexible peripheral wall which is bent in such a way that it can overlap the outer peripheral surface of the catheter part and the outer peripheral surface of the bumper part, wherein a catheter insertion opening into which the catheter part can be inserted is formed in said peripheral wall; a flexible first connecting part for connecting the catheter part and the bumper part in such a way as to extend in the axial direction; and a flexible second connecting part for connecting the bumper part and the guide part in such a way as to extend in the axial direction.

15 Claims, 5 Drawing Sheets

(56) References Cited

U.S. PATENT DOCUMENTS

| | | |
|---|---|---|
| 2008/0269781 A1 | 10/2008 | Funamura et al. |
| 2009/0287157 A1 | 11/2009 | Funamura |
| 2010/0057013 A1 | 3/2010 | Harada |

FOREIGN PATENT DOCUMENTS

| | | |
|---|---|---|
| EP | 2255775 A2 | 12/2010 |
| JP | 2003-290320 A | 10/2003 |
| JP | 2005-168979 A | 6/2005 |
| JP | 2006-296794 A | 2/2006 |
| JP | 2009-183437 A | 8/2009 |
| JP | 2009-273608 A | 11/2009 |
| JP | 2010-273846 A | 12/2010 |

OTHER PUBLICATIONS

International Search Report and Written Opinion dated Feb. 1, 2013 for corresponding PCT Application No. PCT/US2012/055019.

Examination Report from Canadian Patent Office dated Oct. 7, 2014 for corresponding Canadian Patent Application No. 2,848,497.

Extended Search Report issued by the European Patent Office, dated May 11 2015, from counterpart EP Application No. 12832164.3.

* cited by examiner

FISTULA CATHETER AND RELATED METHODS THEREFOR

FIELD

The present invention relates to a fistula catheter used to supply a fluid such as liquid food or nutrients to the alimentary canal of a patient.

BACKGROUND

It is conventional to use a fistula catheter to administer enteral feeding whereby liquid foods or nutrients are supplied to a person who has a reduced capacity to ingest food orally due to, for example, advanced age or illness (referred to below as a "patient"). When enteral feeding is administered, a fistula is established in the patient's abdominal region (gastric fistula), the fistula catheter is fitted in the fistula, and the patient is supplied with the liquid foods through the fistula catheter.

The fistula catheters can be broadly divided into what are known as balloon-type and bumper-type fistula catheters, according to the shape of the intracorporeal fixing part placed inside the body. For example, when a balloon-type intracorporeal fixing part is fitted in a fistula, the balloon is inserted into the fistula in a narrowed, deflated configuration. A syringe can be used to inject air or physiological saline into and inflate the inserted balloon, which serves as an intracorporeal fixing part. When the balloon-type intracorporeal fixing part is to be withdrawn from the fistula, the procedure is reversed. As disclosed, for example, in JP2009-183437A, when a bumper-type intracorporeal fixing part is fitted in a fistula, the bumper is inserted into the fistula in a narrowed state of extension by using a rod-shaped extension tool. The extension tool is then removed from the bumper which has been inserted into the body, whereby the bumper is restored to its original expanded shape and is made to function as an intracorporeal fixing part. When a bumper-type intracorporeal fixing part is withdrawn, the fitting procedure is carried out in reverse.

SUMMARY

The fistula catheter can be fitted in the fistula in the manner described above once the fistula has been made, and subsequently it has to be replaced after a long period of use (around 1 to 4 months, for example). However, when a conventional fistula catheter is replaced, it is necessary to have replacement tools ready, namely a syringe in the case of a balloon-type fistula catheter and an extension tool in the case of a bumper-type fistula catheter.

A special replacement tool of the above kind is preferably used for each patient from the point of view of hygiene, but ensuring that each patient has a replacement tool of the above kind creates a lot of work for a practitioner. Furthermore, there are also times when the fistula catheter is replaced at home, and since the fistula catheter is normally replaced once every 1 to 4 months or so, it is possible that the replacement tool will have been lost. Furthermore, the procedure when using the replacement tool (extension tool) for a conventional bumper-type fistula catheter is especially complicated, so the medical practitioner needs adequate instruction, which also increases the medical practitioner's workload.

Furthermore, there are conventional bumper-type fistula catheters which are larger in diameter than a fistula, even when the bumper has been extended and narrowed, so there is a risk of damaging the fistula, and a less invasive fistula catheter would be preferable.

The present invention has been devised in order to resolve issues such as those described above, and provides a fistula catheter which can be inserted and withdrawn without the use of a replacement tool such as a syringe or an extension tool. The present invention can also provide a fistula catheter that is sparingly invasive for the fistula.

The fistula catheter according to the present invention can comprise a substantially cylindrical catheter part; a rod-like bumper part; a guide part provided with a flexible peripheral wall which is bent in such a way that it can overlap the outer peripheral surface of the catheter part and the outer peripheral surface of the bumper part, wherein a catheter insertion opening into which the catheter part can be inserted is formed in said peripheral wall; a flexible first connecting part for connecting the catheter part and the bumper part in such a way as to extend in the axial direction; and a flexible second connecting part for connecting the bumper part and the guide part in such a way as to extend in the axial direction.

The fistula catheter according to the present invention can comprise a guide part which can overlap the outer peripheral surfaces of the catheter part and the bumper part, and the bumper part and the guide part can be inserted into and withdrawn from a fistula along the guide part. It is therefore possible to obtain a fistula catheter which can be inserted into and withdrawn from a fistula without the use of a replacement tool. Furthermore, it is the bumper part or the catheter part, with the guide part overlapping, which passes through the fistula, and this is less invasive for the fistula.

One or more aspects of the present invention can be directed to a fistula catheter, comprising a cylindrical catheter part; a rod-shaped bumper part; a guide part with a flexible peripheral wall which is bent in such a way that it can overlap the outer peripheral surface of the catheter part and the outer peripheral surface of the bumper part, wherein a catheter insertion opening into which the catheter part can be inserted is formed in said peripheral wall; a flexible first connecting part for connecting the catheter part and the bumper part in such a way as to extend in the axial direction; and a flexible second connecting part for connecting the bumper part and the guide part in such a way as to extend in the axial direction. The bumper part and the catheter part can be inserted and withdrawn along the guide part. The bumper part and the guide part can be insertable into the fistula in the axial direction with the second connecting part bent and the bumper part and guide part overlapping; and the first connecting part and the catheter part can be further insertable into the fistula along the guide part. The bumper part can be suspendable along an inside surface of the wall of an internal organ by means of the first connecting part and the second connecting part so that the bumper part serves as an intracorporeal fixing part. The base-end side of the catheter part and the catheter insertion opening of the guide part can be configured to be exposed on the body-surface side when the bumper part has been made indwelling inside an internal organ wall; and the guide part can be exposed on a body-surface side is bent and the base-end side of the catheter part can be inserted into the catheter insertion opening. The guide part can function as an extracorporeal fixing part. The bumper part can comprise a cylindrical member having a lumen. A rigid core member can be insertable into the lumen of the cylindrical member. The catheter part, the bumper part, the guide part, the first connecting part and the second connecting part can comprise a single member or be formed as a single member. The peripheral wall of the tube member can be partially cut away in the circumferential direction in order to form the guide part, first connecting part and second connecting part, from a single or unitary member. Multiple catheter insertion openings can be provided in the guide part.

One or more further aspects of the invention can be directed to a method of facilitating use of a fistula catheter. The method, in accordance with one or more embodiments relevant to one or more aspects of the invention can comprise providing a fistula catheter comprising a cylindrical catheter part; a rod-shaped bumper part; a guide part with a flexible peripheral wall configured to overlap the outer peripheral surface of the catheter part and the outer peripheral surface of the bumper part and having a catheter insertion opening in said peripheral wall, wherein the catheter part can be inserted into the catheter insertion opening; a flexible first connecting part for connecting the catheter part and the bumper part in such a way as to extend in the axial direction; and a flexible second connecting part configured to connect the bumper part and the guide part in the axial direction.

DETAILED DESCRIPTION

Figure 1:
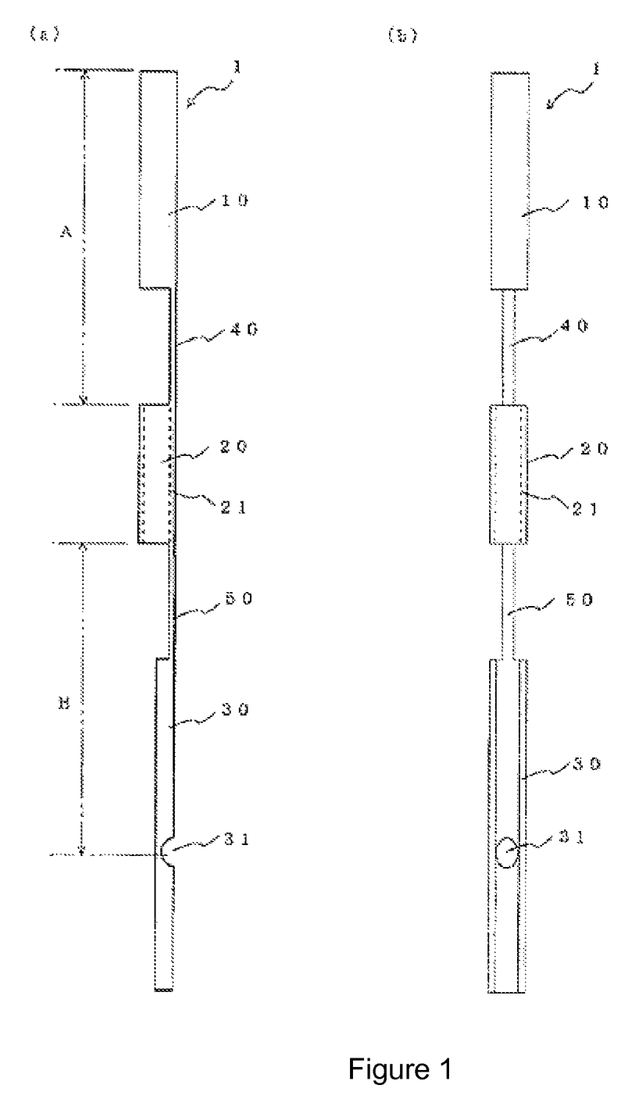
FIG. 1 shows a side view and a plan view of a fistula catheter according to Mode of Embodiment 1.
Figure 2:
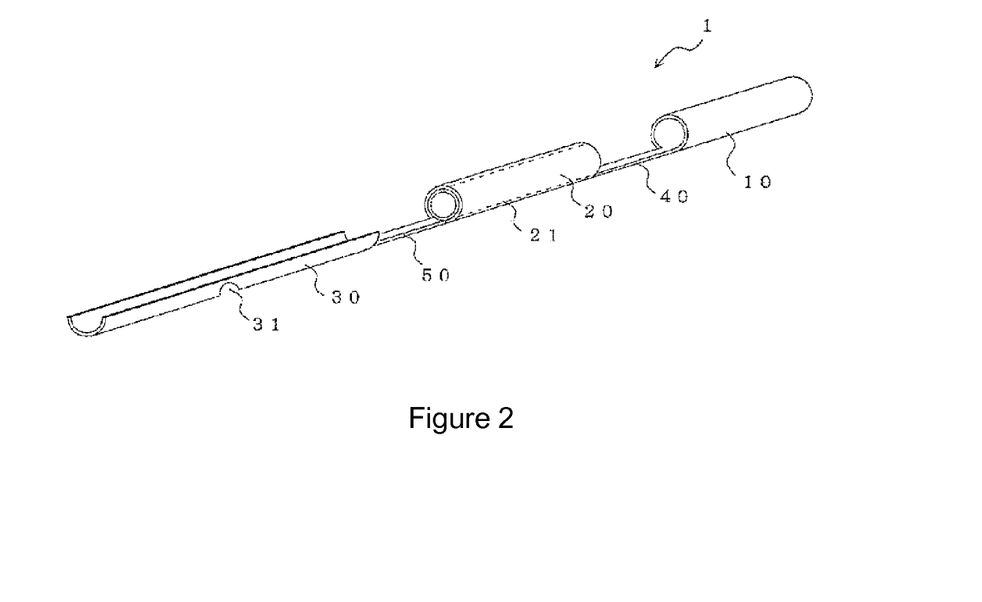
FIG. 2 is an oblique view of the fistula catheter according to Mode of Embodiment 1.
Figure 3:
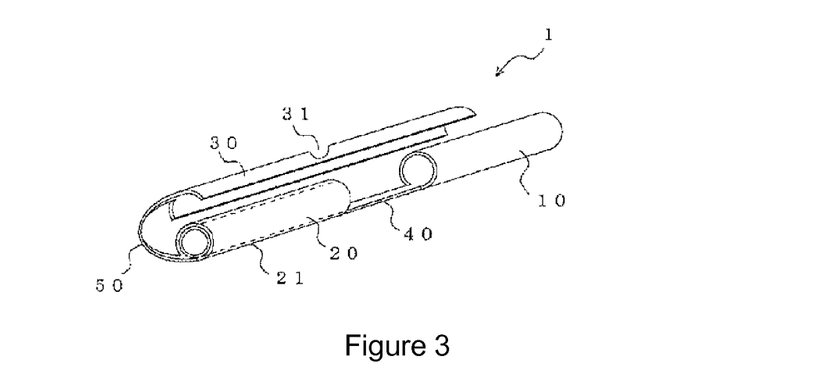
FIG. 3 is an oblique view showing the situation when the fistula catheter according to Mode of Embodiment 1 has been deformed.
Figure 4:
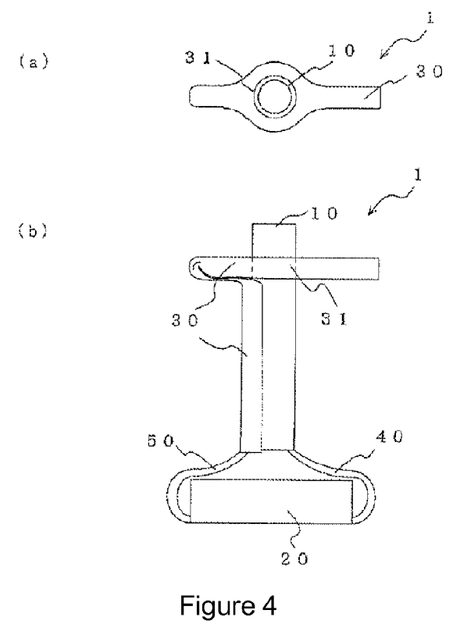
FIG. 4 illustrates the situation when the fistula catheter according to Mode of Embodiment 1 is indwelling in a fistula.

Modes of embodiment of the fistula catheter according to the present invention will be described below with reference to the figures. It should be noted that the present invention is not limited by these modes of embodiment.
Embodiment 1
FIG. 1 exemplarily shows a side view and a plan view of a fistula catheter according to Mode of Embodiment 1, where FIG. 1(a) shows a side view and FIG. 1(b) shows a plan view. FIG. 2 exemplarily shows an oblique view of the fistula catheter according to Mode of Embodiment 1. FIG. 3 exemplarily shows an oblique view when the fistula catheter has been deformed. FIG. 4 exemplarily illustrates the fistula catheter according to Mode of Embodiment 1 indwelling in a fistula. It should be noted that the size relationships among the various members in the figures may differ from those of the actual fistula catheter. Furthermore, components bearing the same reference numbers denote components which are the same or corresponding in FIGS. 1 to 3 and figures to be described later, and these will be common to said components throughout the whole specification.

A fistula catheter 1 can comprise a catheter part 10, a bumper part 20, a guide part 30, a first connecting part 40 and a second connecting part 50. It should be noted that in the following description, the catheter part 10 end or region of the fistula catheter 1 (the top of the page in FIG. 1) may be referred to as the "base-end side" and the guide part 30 end or region may be referred to as the "tip-end side."

The catheter part 10 is inserted into the fistula and typically has the function of allowing the passage of fluids such as nutrients. The catheter part 10 typically has an internal lumen for allowing the passage of fluid, and typically both ends thereof are substantially cylindrical members which are perforated. The catheter part 10 can be made of a flexible synthetic resin material such as polyurethane resin, polyvinyl chloride resin or silicone resin.

The bumper part 20 is to be positioned inside the wall of an internal organ (the stomach wall) of the patient when the fistula catheter 1 has been fitted in the fistula, and it functions as an intracorporeal fixing part for preventing the fistula catheter 1 from being removed from the fistula. The bumper part 20 can be a rod-like or rod-shaped member comprising a cylindrical tube material, which can be made of a synthetic resin material such as polyurethane resin, polyvinyl chloride resin, silicone resin, ABS resin or polyethylene resin, for example. Furthermore, in Mode of Embodiment 1, a core member 21 is typically inserted into the lumen of the bumper part 20. The core member 21 can be a rigid, substantially cylindrical member, and can be disposed in such a way as to be in close contact with the inner wall of the tube forming the bumper part 20. The core member 21 is made of a rigid material such as titanium, polypropylene, polycarbonate or ABS, for example. It should be noted that a configuration may be adopted in which the core member 21 is not provided in the lumen of the bumper part 20. In this variant configuration, the bumper part 20 is preferably made of a rigid material, or a coating is preferably applied to harden or increase the stiffness of the bumper part 20, and the provision of a lumen in the bumper part 20 is optional.

Figure 6:
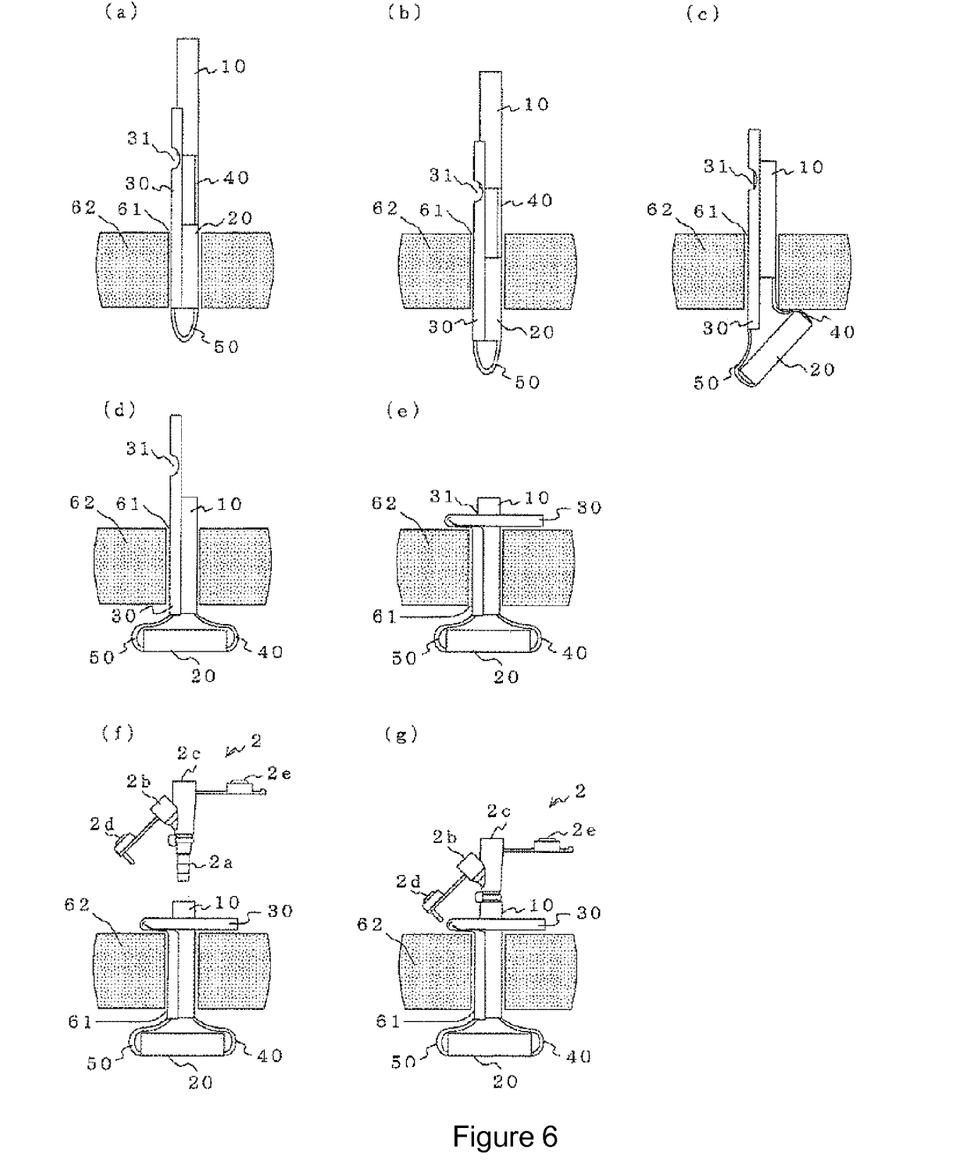
FIG. 6 illustrates the action of the fistula catheter according to Mode of Embodiment 1.

The guide part 30 is typically a flexible member having a shape such that an elongate member can be curved in such a way that the cross section thereof is substantially arc-shaped. The inner peripheral surface of the guide part 30 preferably comprises a curved surface with a degree or radius of curvature that is substantially the same as degree or radius of curvature of the outer peripheral surfaces of the catheter part 10 and the bumper part 20, so that it can overlap the outer peripheral surfaces of the catheter part 10 and the bumper part 20. Moreover, even if the inner peripheral surface of the guide part 30 and the outer peripheral surfaces of the catheter part 10 and the bumper part 20 comprise differently curved surfaces, the guide part 30 can be made of a flexible material, so the flexibility thereof allows it to follow or conform to the outer peripheral surfaces of the catheter part 10 and the bumper part 20. The thickness of the peripheral wall of the guide part 30, the peripheral length, and the curvature of the inner peripheral surface are preferably set in such a way that a state in which the guide part 30 overlaps the outer peripheral surfaces of the catheter part 10 and the bumper part 20 (the state exemplarily shown in FIG. 6(a), to be described later) can be maintained without any support from the hands, for example. This facilitates the operation of insertion into the fistula. In Mode of Embodiment 1, for example, a configuration is adopted in which the cross-sectional shape orthogonally relative to the axial direction of the guide part 30 is a semicircular arc; but if the centre angle of the cross-sectional arc of the guide part 30 is increased, it is possible to increase the level of engagement of the guide part 30, catheter part 10 and bumper part 20. The guide part 30 is typically made of a synthetic resin material such as polyurethane resin, polyvinyl chloride resin or silicone resin, for example.

A catheter insertion opening 31 is formed in the guide part 30. As exemplarily shown in FIG. 4, the catheter part 10 is inserted into the catheter insertion opening 31 while inserted into the fistula. The catheter insertion opening 31 can be an opening which allows the insertion of the catheter part 10, and it may be a circular opening, as shown in the examples of FIGS. 1 to 3, or it may be a slit or notch. The opening diameter of the catheter insertion opening 31 is preferably set in such a way that the outer peripheral surface of the catheter part 10 is in close contact with the catheter insertion opening 31, so that the catheter part 10 which has been inserted into the catheter insertion opening 31 does not readily move.

The first connecting part 40 can be a member for connecting one end of the catheter part 10 (the end on the tip-end side) and one end of the bumper part 20 (the end on the base-end side). The first connecting part 40 is typically a flexible member which can be curved, and can be made of a synthetic resin material such as polyurethane resin, polyvinyl chloride resin or silicone resin, for example.

The second connecting part 50 is typically a member for connecting one end of the bumper part 20 (the end on the tip-end side) and one end of the guide part 30 (the end on the base-end side). The second connecting part 50 is typically a flexible member which can be curved, and can be made of a synthetic resin material such as polyurethane resin, polyvinyl chloride resin or silicone resin, for example.

As shown in FIG. 3, the second connecting part 50 can be bent in order to make the inner peripheral surface of the guide part 30 overlap the outer peripheral surfaces of the catheter part 10 and the bumper part 20. Typically, the curved inner peripheral surface of the guide part 30 suitably engages with the outer peripheral surfaces of the catheter part 10 and the bumper part 20, and a state is maintained in which the guide part 30 overlaps the bumper part 20. The size relationships in the fistula catheter 1 will be described next with reference to FIG. 1.

The longitudinal length of the catheter part 10 is typically substantially the same as the length of the catheter part of a conventional bumper-type fistula catheter, and is in a range of 1.5 cm-7 cm to match the thickness of the patient's abdominal wall.

The longitudinal length of the bumper part 20 is typically greater than the diameter of the fistula in order to prevent withdrawal therefrom, and is in a range of 2 cm-5 cm, for example.

The length A from the base end of the bumper part 20 to the base end of the catheter part 10 (the length including the catheter part 10 and the first connecting part 40) and the length B from the centre of the catheter insertion opening 31 in the guide part 30 to the tip end of the bumper part 20 typically has a size relationship such that when the base end of the catheter part 10 is inserted into the catheter insertion opening 31, the bumper part 20 is suspended substantially horizontally inside the internal organ wall, as exemplarily shown in FIG. 4.

The production of the fistula catheter 1 will be described next.

Figure 5:
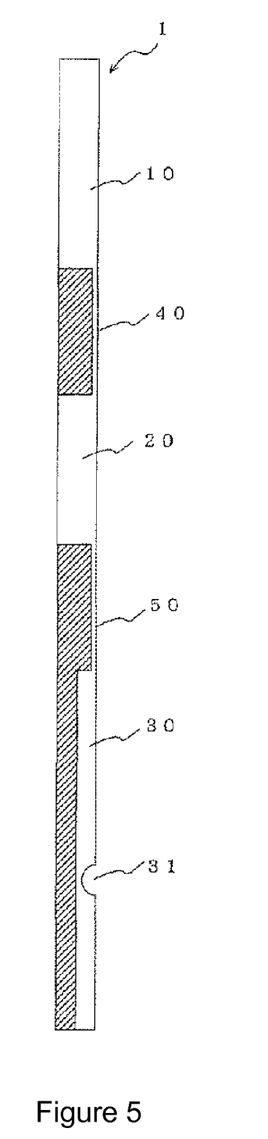
FIG. 5 illustrates the structure of the fistula catheter according to Mode of Embodiment 1.

FIG. 5 illustrates the structure of the fistula catheter according to Mode of Embodiment 1. As shown in FIG. 5, the fistula catheter 1 can comprise, consist essentially of or consist of a single tube member (pipe) whereof the peripheral wall is cut away in order to form the catheter part 10, bumper part 20, guide part 30, first connecting part 40 and second connecting part 50. In FIG. 5, the section where the peripheral wall is cut away and removed is shaded. As shown in the figure, the peripheral wall of the tube between the catheter part 10 and the bumper part 20 is partially cut away in the circumferential direction, and the remaining part of the tube forms the first connecting part 40. The peripheral wall of the tube between the bumper part 20 and the guide part 30 is likewise partially cut away in the circumferential direction, and the remaining part of the tube forms the second connecting part 50. The width of the first connecting part 40 and the second connecting part 50 may be appropriately determined to take account of flexibility to allow bending and durability such that breakage is unlikely to occur even after several months of use with the fistula catheter fitted in the fistula. The guide part 30 can be formed by partially cutting away the peripheral wall of the tube in the circumferential direction. The catheter insertion opening 31 can be formed in the peripheral wall of the guide part 30.

The action of the fistula catheter according to Mode of Embodiment 1 will be described next.

FIG. 6 exemplarily illustrates the action of the fistula catheter according to Mode of Embodiment 1. FIGS. 6(a)-(g) show the procedure for fitting the fistula catheter 1 in the patient's fistula once the fistula has been made or when the fistula catheter 1 which is placed in the fistula is being replaced. The fistula 61 formed in the patient and the body wall 62 (internal organ wall, such as stomach wall, and abdominal wall) are shown together in FIG. 6.

As shown in FIG. 6(a), the fistula catheter 1, which is in a state in which the second connecting part 50 is bent so that the inner peripheral surface of the guide part 30 overlaps the outer peripheral surface of the bumper part 20, is inserted into the patient's fistula 61 with the second connecting part 50 oriented downward (the patient side). The outer peripheral surface of the bumper part 20 is inserted along the inner peripheral surface of the guide part 30, so the bumper part 20 can be inserted directly and smoothly. The diameter of the portion which is inserted into the fistula 61 is typically the diameter of the guide part 30 overlapping the bumper part 20, which is smaller than the diameter of a conventional bumper-type intracorporeal fixing part which has been extended, and it is less invasive in the fistula 61.

As shown in FIG. 6(b), the overlapping portion of the bumper part 20 and the guide part 30 is typically pushed down into the fistula 61, and an endoscope is used to confirm that the bumper part 20 has reached inside the internal organ wall such as the stomach wall.

As shown in FIG. 6(c), the first connecting part 40 and the catheter part 10 are typically inserted into the fistula 61 along the inner peripheral surface of the guide part 30 while the position of the guide part 30 is fixed on the body-surface side. The outer peripheral surface of the catheter part 10 typically follows the inner peripheral surface of the guide part 30, so the catheter part 10 can be inserted smoothly and directly into the fistula 61. The maximum diameter of the portion which is inserted into the fistula 61 is typically the diameter of the guide part 30 overlapping the diameter of the catheter part 10, so an increase in the diameter of the catheter part 10 is minimized, which is less invasive for the fistula 61. When the catheter part 10 is pushed further into the fistula 61, the bumper part 20 is separated from the guide part 30 inside the internal organ wall.

When the catheter part 10 is then pushed further into the fistula 61 until the tip end of the catheter part 10 reaches inside the internal organ wall, the configuration shown in FIG. 6(d) is achieved. As shown in FIG. 6(d), the bumper part 20 can be in a state in which it is suspended from the catheter part 10 and guide part 30 by means of the first connecting part 40 and the second connecting part 50. At this point, the bumper part 20 can have a substantially horizontal orientation and can function as retainer (intracorporeal fixing part) for the fistula 61.

Furthermore, in Mode of Embodiment 1, the core member 21 is provided in the lumen of the tube of the bumper part 20, so the shape of the bumper part 20 is maintained in a substantially linear shape inside the internal organ wall. This means that even if the fistula catheter 1 is pulled in the direction of withdrawal from the body-surface side, for example, it is possible to suppress folding of the bumper part 20 which would then be pulled into the fistula 61, and the fixed state can be maintained.

The sizes of the members are set in such a way that while the bumper part 20 is suspended substantially horizontally inside the internal organ wall (FIG. 6(*d*)), there is a positional relationship such that part of the base end of the catheter part 10, a prescribed length of the guide part 30, and the catheter insertion opening 31 are exposed on the body-surface side.

The guide part 30 which is projecting on the body-surface side can then be folded and the base end of the catheter part 10 can be inserted into the catheter insertion opening 31, as shown in FIG. 6(*e*). By doing so, the catheter part 10 and the guide part 30 can be made into a single piece on the body-surface side. The guide part 30 which is in this state typically extends in a direction substantially orthogonal to the axial direction of the catheter part 10 while following the surface of the body, and it can function as a retainer (extracorporeal fixing part) for suppressing pulling of the catheter part 10 into the body from the fistula 61.

Fitting of the fistula catheter 1 into the fistula 61 can be completed by means of the above procedure. It should be noted that a guidewire may be inserted into the fistula 61 beforehand. The guidewire may be inserted into the lumen of the bumper part 20 and catheter part 10 in order to insert the bumper part 20 and catheter part 10 into the fistula 61 along the guidewire, not shown in FIG. 6. By doing so, the fistula catheter 1 can be fitted into the fistula 61 with greater certainty.

As shown in FIG. 6(*f*), an adapter 2 can be attached to the catheter part 10. The adapter 2 can be a member for connecting the catheter part 10 and a tube (not depicted) for supplying fluids such as nutrients or drug solutions. FIG. 6 shows an example of an adapter 2 comprising a ribbed insertion part 2*a* which is inserted into the catheter part 10, two injection ports 2*b*, 2*c*, and caps 2*d*, 2*e* corresponding to each injection port, but any adapter 2 suitable for the intended application may be used.

FIG. 6(*g*) shows a state in which the adapter 2 is attached to the fistula catheter 1. When nutrients or drug solutions are to be injected, the caps 2*d*, 2*e* typically are removed; a syringe or tube (not depicted) is connected to the injection ports 2*b*, 2*c*; and nutrients or drug solutions are injected. As a result, the injected nutrients or drug solutions can be introduced inside the internal organ wall from the tip end of the catheter part 10 which lies inside the internal organ wall, via the lumen of the catheter part 10.

It should be noted that the fistula catheter 1 can be withdrawn from the fistula 61 by carrying out the procedure in reverse. For example, the adapter 2 is typically removed (FIG. 6(*g*), (*f*)); the guide part 30 is typically raised; the catheter part 10 is typically withdrawn from the catheter insertion opening 31 (FIG. 6(*e*), (*d*)); and the catheter part 10 is pulled out in the direction away from the fistula 61 along the guide part 30 which is inserted in the fistula 61 (FIG. 6(*c*)). By doing so, the bumper part 20 moves from a substantially horizontal state to an upright state which can pass through the fistula 61, and the guide part 30 and the bumper part 20 can both be withdrawn from fistula 61 (FIGS. 6(*c*), (*b*), (*a*)).

The fistula catheter in accordance with one or more aspects of the present invention can be fitted to or withdrawn from the fistula using just the fistula catheter, without the use of another tool. This means that there is no need for a medical practitioner to utilize a replacement tool such as a syringe or extension tool, as would be required conventionally, and it is possible to reduce the number of tools which the medical practitioner or facility has to employ. Furthermore, the fistula catheter can be fitted into and withdrawn from the fistula by means of a simple procedure and without the use of any other tools, so it is possible to reduce the workload of the practitioner. The fistula catheter in accordance with one or more aspects of the present invention can be fitted into and withdrawn from the fistula using a simple procedure, and therefore the operation time can be shortened and the burden on both the practitioner and the patient can be reduced. Furthermore, the fistula catheter in accordance with one or more aspects of the present invention makes it possible for the bumper part and catheter part to be inserted into and withdrawn from the fistula along the guide part which has a rounded peripheral wall. The guide part in accordance with one or more aspects of the present invention can therefore serve to protect the fistula, and the fistula is irritated to a lesser extent when the bumper part and catheter part are inserted into or withdrawn from the fistula.

Furthermore, the diameter of the portion of the fistula catheter, in accordance with one or more aspects of the present invention, which passes through the fistula is about the diameter of the guide part overlapping the bumper part or the diameter of the guide part overlapping the catheter part, so the diameter is smaller than would be the case when a conventional bumper-type intracorporeal fixing part is extended. The bumper part 20 can therefore be made less invasive for the fistula compared to a conventional bumper-type intracorporeal fixing part.

Furthermore, in accordance with one or more aspects of the present invention, the fistula catheter can comprise a single tube (pipe) or a unitary piece. If different members are bonded together, for example, there is a risk of the bonded sections becoming detached, but this risk can be eliminated with the fistula catheter in accordance with one or more aspects of the present invention. It should be noted that an example was described in Mode of Embodiment 1 in which the peripheral wall of a single tube is cut away in order to form the fistula catheter 1; however, one or more further aspects of the present invention can involve forming the fistula catheter 1 by combining multiple members. For example, the catheter part 10, first connecting part 40, second connecting part 50 and guide part 30 may each be made of polyurethane resin or silicone resin, while the bumper part 20 may be made of ABS resin or polyethylene resin, and these members may be joined by bonding or welding.

Embodiment 2

Figure 7:
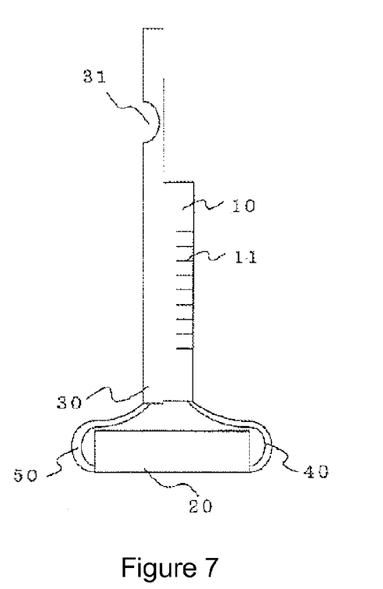
FIG. 7 illustrates a fistula catheter according to Mode of Embodiment 2.

FIG. 7 exemplarily illustrates a fistula catheter according to Mode of Embodiment 2. The description of Mode of Embodiment 2 will focus on the differences with Mode of Embodiment 1, without further discussion to common features therebetween.

Calibrations 11 can be provided on the catheter part 10 of the fistula catheter 1 shown in FIG. 7. The calibrations 11 typically show the depth of insertion of the catheter part 10 into the fistula 61. By providing these calibrations 11, the practitioner can ascertain the extent of insertion of the catheter part 10 into the fistula 61 and can perform a smooth fitting operation.

Embodiment 3

Figure 8:
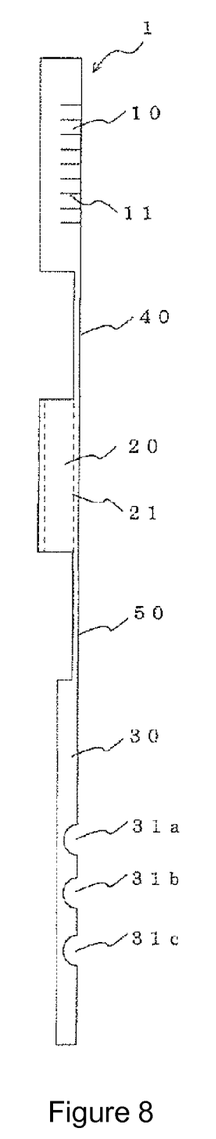
FIG. 8 illustrates a fistula catheter according to Mode of Embodiment 3.

FIG. 8 exemplarily illustrates a fistula catheter according to Mode of Embodiment 3. The fistula catheter according to Mode of Embodiment 3 makes it possible to deal with multiple thicknesses of the body wall. The description of Mode of Embodiment 3 will focus on the differences with Mode of Embodiment 1, without further discussion to common features therebetween.

As shown in FIG. 8, multiple catheter insertion openings 31*a*, 31*b*, 31*c* can be provided in the guide part 30. The catheter insertion openings 31*a*, 31*b*, 31*c* can be formed at prescribed intervals in the axial direction of the guide part 30. It should be noted that FIG. 8 shows an example in which three catheter insertion openings are provided but the number of catheter insertion openings is not limited to this configuration.

The calibrations 11 can be provided on the catheter part 10 in the same way as in Mode of Embodiment 2.

Figure 9:
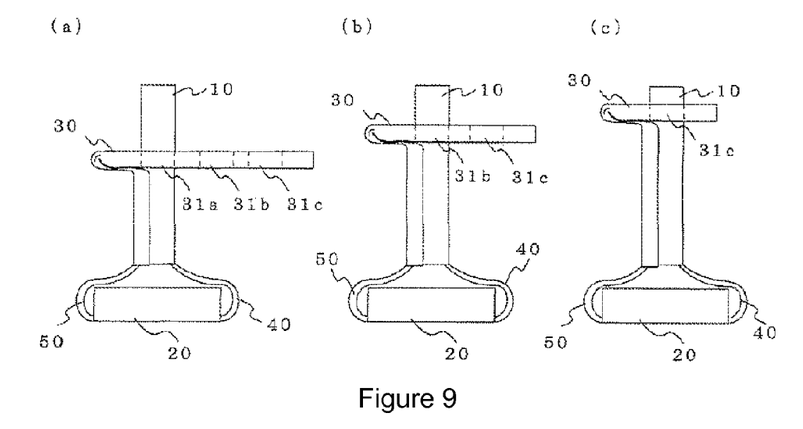
FIG. 9 illustrates the action of the fistula catheter according to Mode of Embodiment 3.

FIG. 9 exemplarily illustrates the action of the fistula catheter according to Mode of Embodiment 3. FIGS. 9(*a*), (*b*), (*c*) show the situation when the catheter part 10 is inserted into the catheter insertion openings 31*a*, 31*b*, 31*c*. As shown in FIG. 9, the fistula catheter can be inserted into the patient's fistula, after which the catheter part 10 which is exposed on the body-surface side can be inserted into any of the catheter insertion openings 31*a*, 31*b*, 31*c*. When the catheter part 10 is inserted into any of the catheter insertion openings 31*a*, 31*b*, 31*c* in this way, it is possible to vary the distance from the bumper part 20 to the surface of the body, so it is possible to deal with patients having varying thicknesses of body wall. Any of the catheter insertion openings 31*a*, 31*b*, 31*c* can be selected for insertion of the catheter part 10 to match the thickness of the patient's body wall. In this case, the practitioner can ascertain the insertion depth of the catheter part 10 by referring to the calibrations 11 provided on the catheter part 10, and can determine which of the catheter insertion openings 31*a*, 31*b*, 31*c* to be used.

As described above, Mode of Embodiment 3 demonstrates an advantage in that it is possible to obtain a fistula catheter to deal with patients having varying thicknesses of body wall, in addition to the same advantages as Mode of Embodiment 1.

TABLE 1

| Key to Symbols | |
|---|---|
| 1 | fistula catheter |
| 2 | adapter |
| 2a | insertion part |
| 2b | injection port |
| 2c | injection port |
| 2d | cap |
| 2e | cap |
| 10 | catheter part |
| 11 | calibrations |
| 20 | bumper part |
| 21 | core member |
| 30 | guide part |
| 31 | catheter insertion opening |
| 31a | catheter insertion opening |
| 31b | catheter insertion opening |
| 31c | catheter insertion opening |
| 40 | first connecting part |
| 50 | second connecting part |
| 61 | fistula |
| 62 | body wall. |

The invention claimed is:

1. A fistula catheter, comprising:
a cylindrical catheter part extending in an axial direction;
a rod-shaped bumper part;
a guide part with a flexible peripheral wall bent to provide a shape configured to overlap the outer peripheral surface of the catheter part and the outer peripheral surface of the bumper part, wherein a catheter insertion opening configured to receive the catheter part therein is formed in said peripheral wall;
a flexible first connecting part for connecting the catheter part and the bumper part in such a way as to extend in the axial direction; and
a flexible second connecting part for connecting the bumper part and the guide part in such a way as to extend in the axial direction.

2. The fistula catheter according to claim 1, wherein the bumper part and the catheter part are configured to be inserted into a fistula and withdrawn from the fistula when positioned along the guide part.

3. The fistula catheter according to claim 1, wherein the bumper part and the guide part are insertable into the fistula in the axial direction with the second connecting part bent and the bumper part and guide part overlapping; and the first connecting part and the catheter part are further insertable into the fistula along the guide part, whereby the bumper part is suspendable along an inside surface of the wall of an internal organ by means of the first connecting part and the second connecting part so that the bumper part serves as an intracorporeal fixing part.

4. The fistula catheter according to claim 1, wherein the base-end side of the catheter part and the catheter insertion opening of the guide part are configured to be exposed on the body-surface side when the bumper part has been made indwelling inside an internal organ wall; and the guide part is exposed on a body-surface side is bent and the base-end side of the catheter part is inserted into the catheter insertion opening, whereby the guide part functions as an extracorporeal fixing part.

5. The fistula catheter according to claim 1, wherein the bumper part comprises a cylindrical member having a lumen; and a rigid core member is insertable into the lumen of the cylindrical member.

6. The fistula catheter according to claim 1, wherein the catheter part, the bumper part, the guide part, the first connecting part and the second connecting part comprise a single member.

7. The fistula catheter according to claim 6, wherein the peripheral wall of the single member is partially cut away in the circumferential direction in order to form the guide part, first connecting part and second connecting part.

8. The fistula catheter according to claim 1, characterized in that multiple catheter insertion openings are provided in the guide part.

9. The fistula catheter according to claim 1, wherein the first flexible connecting part and the flexible second connecting part are configured to permit the bumper part to be located orthogonal to the axial direction with at least a portion of the guide part overlapping the outer peripheral surface of the catheter part.

10. The fistula catheter according to claim 1, wherein the guide part is configured for the flexible peripheral wall to overlap the outer peripheral surface of the catheter part and the outer peripheral surface of the bumper part with the guide part extending in the axial direction.

11. The fistula catheter according to claim 1, wherein at least a portion of the guide part is oriented in a direction substantially perpendicular to the axial direction with the catheter part inserted in the catheter insertion opening.

12. A method of facilitating use of a fistula catheter, comprising: providing a fistula catheter comprising a cylindrical catheter part extending in an axial direction; a rod-shaped bumper part; a guide part with a flexible peripheral wall configured to overlap the outer peripheral surface of the catheter part and the outer peripheral surface of the bumper part and having a catheter insertion opening in said peripheral wall, wherein the catheter insertion opening is configured to receive the catheter part therein; a flexible first connecting part for connecting the catheter part and the bumper part in such a way as to extend in the axial direction; and a flexible second connecting part configured to connect the bumper part and the guide part in the axial direction.

13. A fistula catheter, comprising:
a cylindrical catheter part extending in an axial direction;
a rod-shaped bumper part;
a guide part with a flexible peripheral wall bent to provide a shape configured to overlap the outer peripheral surface of the catheter part and the outer peripheral surface of the bumper part, wherein a catheter insertion opening configured to receive the catheter part therein is formed in said peripheral wall;
a flexible first connecting part for connecting the catheter part and the bumper part in such a way as to extend in the axial direction; and
a flexible second connecting part for connecting the bumper part and the guide part in such a way as to extend in the axial direction,
wherein the bumper part and the guide part are insertable into the fistula in the axial direction with the second connecting part bent and the bumper part and guide part overlapping; and the first connecting part and the catheter part are further insertable into the fistula along the guide part, whereby the bumper part is suspendable along an inside surface of the wall of an internal organ by means of the first connecting part and the second connecting part so that the bumper part serves as an intracorporeal fixing part.

14. A fistula catheter, comprising:
a cylindrical catheter part extending in an axial direction;
a rod-shaped bumper part;
a guide part with a flexible peripheral wall bent to provide a shape configured to overlap the outer peripheral surface of the catheter part and the outer peripheral surface of the bumper part, wherein a catheter insertion opening configured to receive the catheter part therein is formed in said peripheral wall;
a flexible first connecting part for connecting the catheter part and the bumper part in such a way as to extend in the axial direction; and
a flexible second connecting part for connecting the bumper part and the guide part in such a way as to extend in the axial direction,
wherein the base-end side of the catheter part and the catheter insertion opening of the guide part are configured to be exposed on the body-surface side when the bumper part has been made indwelling inside an internal organ wall; and the guide part is exposed on a body-surface side is bent and the base-end side of the catheter part is inserted into the catheter insertion opening, whereby the guide part functions as an extracorporeal fixing part.

15. A fistula catheter, comprising:
a cylindrical catheter part extending in an axial direction;
a rod-shaped bumper part;
a guide part with a flexible peripheral wall bent to provide a shape configured to overlap the outer peripheral surface of the catheter part and the outer peripheral surface of the bumper part, wherein a catheter insertion opening configured to receive the catheter part therein is formed in said peripheral wall;
a flexible first connecting part for connecting the catheter part and the bumper part in such a way as to extend in the axial direction; and
a flexible second connecting part for connecting the bumper part and the guide part in such a way as to extend in the axial direction,
wherein the catheter part, the bumper part, the guide part, the first connecting part and the second connecting part comprise a single member, and
wherein the peripheral wall of the single member is partially cut away in the circumferential direction in order to form the guide part, first connecting part and second connecting part.

* * * * *